(12) United States Patent
Prager et al.

(10) Patent No.: US 8,012,094 B2
(45) Date of Patent: Sep. 6, 2011

(54) IMMERSION BAG SYSTEM FOR USE WITH AN ULTRASOUND PROBE

(75) Inventors: Thomas C. Prager, Wimberley, TX (US); Thomas A. Burba, Plymouth, MN (US); David R. Hardten, Orono, MN (US)

(73) Assignee: ESI, Inc., Plymouth, MN (US)

( * ) Notice: Subject to any disclaimer, the term of this patent is extended or adjusted under 35 U.S.C. 154(b) by 1094 days.

(21) Appl. No.: 11/356,873

(22) Filed: Feb. 17, 2006

(65) Prior Publication Data

US 2007/0239030 A1  Oct. 11, 2007

(51) Int. Cl.
*A61B 8/00* (2006.01)

(52) U.S. Cl. ............................................. 600/459

(58) Field of Classification Search .................. 600/437, 600/459, 452; 73/627; 604/163; D24/133, D24/137, 150, 172, 186, 187; 206/316.1, 206/363, 364, 439
See application file for complete search history.

(56) References Cited

U.S. PATENT DOCUMENTS

| | | | | |
|---|---|---|---|---|
| 3,049,001 A | * | 8/1962 | Mackay et al. | 600/405 |
| 4,564,018 A | * | 1/1986 | Hutchison et al. | 600/452 |
| 4,841,979 A | * | 6/1989 | Dow et al. | 600/446 |
| 5,318,029 A | * | 6/1994 | Palese | 600/399 |
| 6,132,378 A | * | 10/2000 | Marino | 600/459 |
| 6,402,695 B1 | * | 6/2002 | Grimm | 600/459 |
| 7,162,291 B1 | * | 1/2007 | Nachaliel | 600/393 |
| 7,287,856 B2 | * | 10/2007 | Prisco | 351/219 |
| 2003/0195420 A1 | * | 10/2003 | Mendlein et al. | 600/437 |
| 2005/0240102 A1 | * | 10/2005 | Rachlin et al. | 600/437 |
| 2006/0241480 A1 | * | 10/2006 | Wilk | 600/466 |

* cited by examiner

*Primary Examiner* — Tse Chen
*Assistant Examiner* — Rochelle Reardon
(74) *Attorney, Agent, or Firm* — Hugh D. Jaeger, Esq.

(57) ABSTRACT

An immersion bag system for use with an ultrasound probe to overcome near field artifact includes a flexible thin wall thickness immersion bag with an attached flexible collar having an integral internal seal. The immersion bag contains a gel or other ultrasound transmission medium and is sealingly and removably attached to the tip end of an ultrasound probe by use of the flexible collar having the integral internal seal. The immersion bag is able to conform to a cornea as well as to other surfaces whether flat or irregular, thereby enabling an ultrasound probe to be used easily on such surfaces. An ultrasound probe in use with the immersion bag system is maintained at a distance above the contact surface of the immersion bag and is positionable about the vertical axis while the immersion bag maintains stationary conformal contact with the structure against which it is in contact.

42 Claims, 10 Drawing Sheets

IMMERSION BAG SYSTEM FOR USE WITH AN ULTRASOUND PROBE

CROSS REFERENCES TO RELATED APPLICATIONS

None.

FIELD OF THE INVENTION

The present invention primarily applies to the medical device field, and more particularly, pertains to an immersion bag system having an immersion bag of acoustically invisible, i.e., transparent, material and a sealing collar with pressure release valve that encapsulates the distal end of and is incorporated into use with an ultrasound probe. The immersion bag system, suitable for containment of a gel or other aqueous medium, overcomes near field artifact allowing the examination of shallow anatomical structures.

Definition of "near field artifact." Typically, a stationary ultrasound probe passes or scans approximately 10 degrees during ultrasound scanning, but by physically moving the ultrasound probe tip back and forth via a motor or other suitable means, a range of 120 degrees can be examined. However, when the ultrasound probe transducer head moves, the consequential pulsating of the ultrasound waves causes the ultrasound waves to collide with one another, thus creating interference which results in an acoustic dead zone. Structures contained within this dead zone cannot be visualized; this is termed "near field artifact". Therefore, examining shallow/superficial tissue with a moving ultrasound probe, anatomical structures within the near field artifact cannot be visualized because of the near field artifact.

This invention has medical and industrial applications by enhancing the ability to exam shallow/superficial structures amenable to ultrasound evaluation. Medical and industrial sonogram examinations may be improved by this method of overcoming near field artifact (defined previously). This includes:

a. anterior ocular structures, e.g., the cornea, iris, lens, ciliary body;
b. skin lesions, e.g., skin cancers, cysts, or neoplasms;
c. vascular structure/flow assessment; and,
d. industrial monitoring of flow characteristics in tubing.

DESCRIPTION OF THE PRIOR ART

Ultrasound scans of the eye or other areas of the body are performed using an ultrasound scan probe and a coupling medium placed between the ultrasound probe tip and the surface of the area being scanned during examination. The medium, such as a gel or other less viscous aqueous medium, allows for the transmission of ultrasound waves between the ultrasound probe and through human tissue or other structures. To reduce or eliminate the near field artifact, the ultrasound probe tip and the superficial structures under examination (such as blood vessels or anterior aspects of the eye) must be separated at a distance from each other and not in direct contact. A common method of accomplishing this is to use a cylinder-shaped cup that is open on both ends and contains a gel or other suitable aqueous medium, which is then placed over the area of the examining surface. The use of an open ended cylinder-shaped cup requires that the operator fill the cup with gel or other suitable aqueous medium. An excessive filling of the cup may result in undesirable overrun of the cup when the tip of the ultrasound probe is introduced therein. An insufficient filling of the cup results in less than desirable ultrasound scan examination because the near field artifact opaque zone cannot be overcome, thus preventing an examination of the structure under study. More importantly, if a cylinder with an open bottom, i.e., a cup, is used, the gel or other suitable aqueous medium must be at a depth to allow a sufficient probe distance from the exam surface to overcome the opaque zone created by the near field artifact. The acoustically transparent immersion bag of the present invention eliminates the need for tedious and correct medium filling to a proper level and provides for ultrasound probe separation from the exam surface to overcome the near field artifact, thereby allowing visualization of superficial structures of the body and/or other structures during the ultrasound exam.

SUMMARY OF THE INVENTION

The general purpose of the present invention is the creation of an immersion bag system, portions of which are fabricated from acoustically invisible, i.e., transparent, material, such as polyethylene, hydrophilic plastic or other suitable thin flexible material, for encapsulating the tip of an ultrasound probe. An immersion bag, suitable for containment of a gel or other aqueous medium, overcomes near field artifact thereby allowing the examination of shallow/superficial structures. The immersion bag is permanently attached to a flexible collar which seals around the distal end of the ultrasound probe outer body.

According to one or more embodiments of the present invention, there is an immersion bag system having a flexible compressible collar and an immersion bag attached thereto which are collectively used to encapsulate the tip portion of an ultrasound probe. The immersion bag system, portions of which can contain preloaded or site-loaded gel or other suitable aqueous medium, engages and surrounds a portion of the distal end of an ultrasound probe to an adequate depth to overcome the near field artifact. The mutually secured immersion bag and flexible collar are comprised of flexible and pliable materials. Specifically, the flexible collar includes an open end for inserting an ultrasound probe and includes an integral seal. The acoustically invisible immersion bag is attached to the flexible collar, each having annular configurations. A lip of the immersion bag is permanently secured within the flexible collar by a capture ring and other suitable attachment means. Additionally, the seal, which is integral to the flexible collar frictionally engages the body of the ultrasound probe upon the ultrasound probe being introduced therein. By inserting the ultrasound probe into the partially liquid filled immersion bag, slight hydraulic (internal) pressure is created, effectively eliminating bag material wrinkles, which is another cause of acoustical near field artifact, thereby forming and ensuring a smooth surface shape of the immersion bag. To maintain immersion bag shape and integrity, venting is provided by one or more self-sealing valves to release air, excess gel, or other excess aqueous medium from the immersion bag during insertion of the ultrasound probe or during operation of the invention in order to maintain positive internal immersion bag pressure. One or more self-sealing valves are calibrated to provide positive internal pressure at a safe immersion bag material limit. The internal pressure and bag tension also provides resistance and tactile feedback to the operator when moving the probe toward the immersion bag bottom. This internal immersion bag pressure and bag tension offsets the ultrasound probe tip from the examined surface, thus overcoming near field artifact and maintaining spacing between the transducer and the immersion bag end. The end of the immersion bag is conformally reshaped to mirror and envelop the examining surface upon contact while remaining wrinkle free. Moreover, being flexible and pliable, the immersion bag conforms to irregularly shaped anatomical areas such as, but not limited to, the nose region or eyelid.

The flexible immersion bag accommodates off-center and angular positioning of the ultrasound probe for off-center ultrasound scans. Thus, while the immersion bag is immobile, the ultrasound probe is free to move within the immersion bag. This minimizes potential damage to sensitive and delicate tissues such as the cornea. The ultrasound probe and immersion bag containing the liquid medium can easily be moved and repositioned on different anatomical areas to be examined.

One significant aspect and feature of the present invention is an acoustically transparent immersion bag of an immersion bag system that encapsulates one end of an ultrasound probe.

Another significant aspect and feature of the present invention includes an acoustically transparent immersion bag system where a collar including a seal and a capture ring in cooperation with an immersion bag surround and engage a portion of an ultrasound probe.

Still another significant aspect and feature of the present invention is a flexible collar and closely associated structure which effectively secures and seals to the ultrasound probe body.

Still another significant aspect and feature of the present invention is an immersion bag which can be preloaded on site with a gel or other aqueous medium.

Yet another significant aspect and feature of the present invention is an immersion bag wherein gel or other aqueous medium is contained and encapsulated about and between the distal end of an ultrasound probe and the interior of the immersion bag.

Another significant aspect and feature of the present invention is a flexible collar including controlled pressure venting for air, gases, gels or other aqueous medium.

Yet another significant aspect and feature of the present invention is a flexible immersion bag that accommodates off-center positioning of an ultrasound probe for off-center ultrasound scans by the immersion bag remaining stationary and the ultrasound probe moving within the immersion bag so that there is no or minimal abrasive contact with delicate or sensitive structures.

Another significant aspect and feature of the present invention is an immersion bag including a flexible collar with one or more self-sealing valves which provide for passive control of the pressure in an immersion bag during probe insertion and thereby prevent the immersion bag from bursting by allowing air and excessive filler medium to escape.

Another significant aspect and feature of the present invention is internal immersion bag hydraulic pressure and bag material tension creating buoyancy and resistance on the ultrasound probe when the operator is moving the probe deeper into the immersion bag and contacting the examined surface. This offsets the height of the ultrasound probe from the examined surface.

Having thus briefly described embodiments of the present invention and having mentioned some significant aspects and features of the present invention, it is the principal object of the present invention to provide an acoustically transparent immersion bag system that overcomes near field artifact by surrounding the tip portion of an ultrasound probe with gel or liquid contained in an immersion bag that is secured to and about the ultrasound probe via a flexible collar that contains self-sealing valve structure for excess air or excess liquid.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
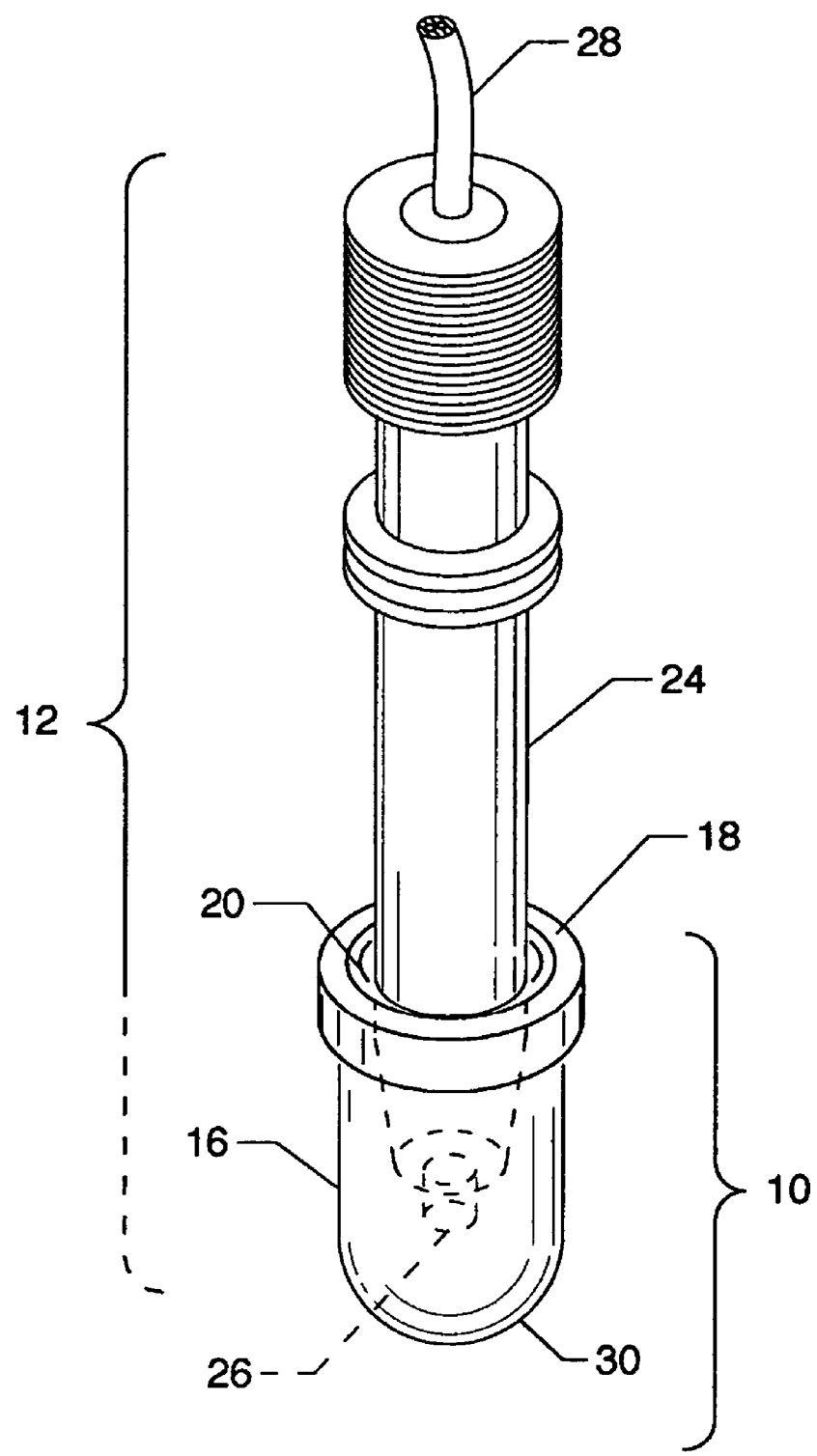
FIG. 1 is an isometric view of an immersion bag system, the present invention, shown in use surrounding the tip of an ultrasound probe.
Figure 2:
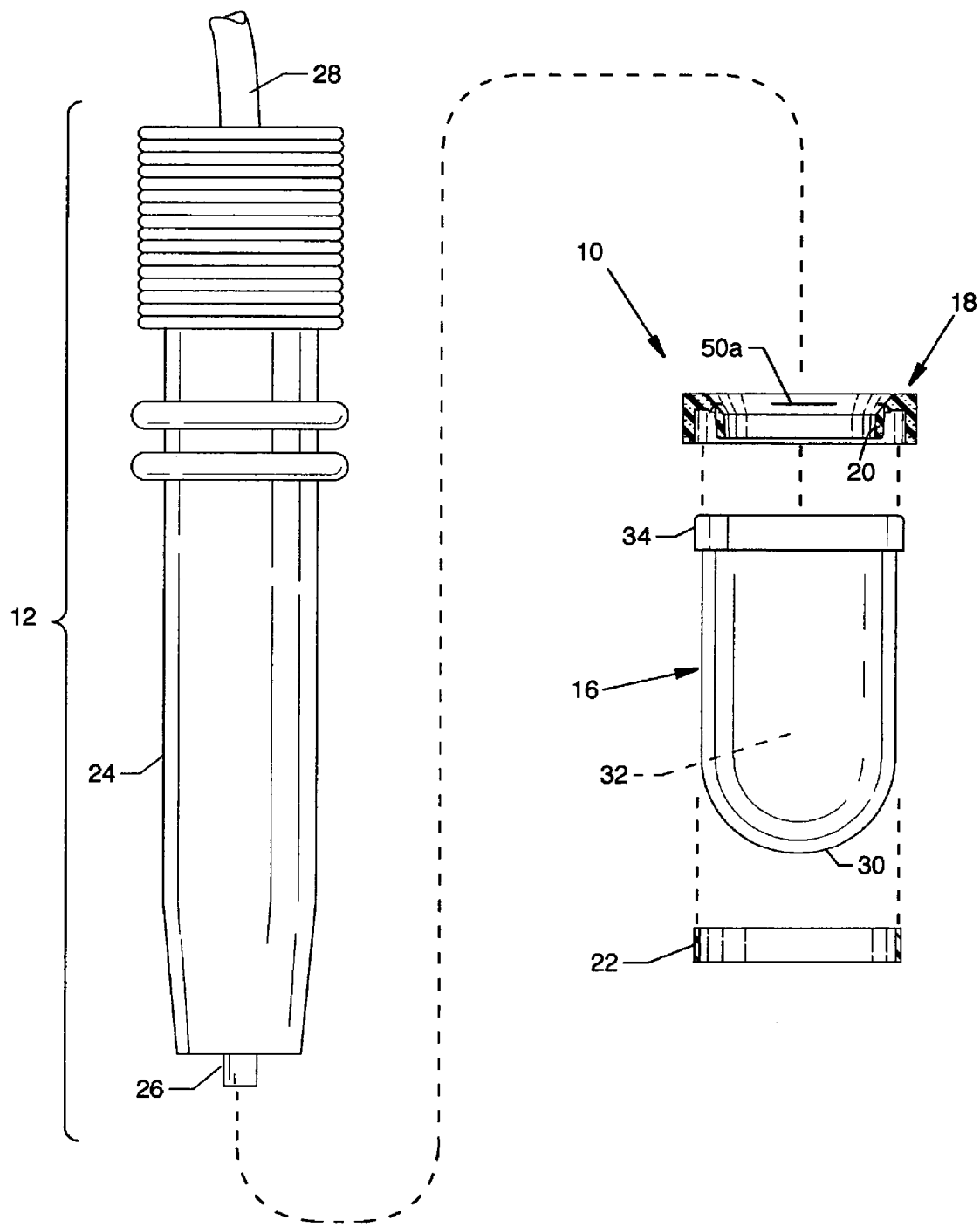
FIG. 2 is a partially exploded view of an immersion bag system and a typical ultrasound probe for use therewith.

FIG. 1 is an isometric view of an immersion bag system 10, the present invention, shown affixed to and in use with an ultrasound probe 12. The lower region of the ultrasound probe 12 is sealed in close association with the following components comprising the immersion bag system 10, each with flexible qualities, including: an immersion bag 16, a flexible collar 18 having an integral seal 20, and a capture ring 22, all of which are shown in FIG. 2. The body 24 of the ultrasound probe 12 generally is tubular in shape and includes a transducer 26 at one end and houses other internal components associated with operation of the transducer 26. The ultrasound probe body 24 includes suitable geometrically configured external structure about the upper region thereof. A control/power cable 28 exits one end of the ultrasound probe 12 for connection to external support components associated with operation of the transducer 26.

FIG. 2 is a partially exploded view of the immersion bag system 10 which in use will frictionally engage the lower portion of the ultrasound body 24. The structure of the immersion bag system 10 includes the immersion bag 16, the flexible collar 18, the seal 20 integral to the flexible collar 18, and the capture ring 22, collectively having features suitable for providing sealed communication of the immersion bag 16 with the lower portion of the body 24 of the ultrasound probe 12.

The seal 20, which is an integral portion of the flexible collar 18, is of annular shape, is fashioned of a flexible material, such as, but not limited to, latex, rubber, plastic, or other suitable material, and includes aligned and connecting generally annular-shaped structure.

The immersion bag 16 is formed of a thin and flexible pliable acoustically transparent material, such as polyethylene, hydrophyllic plastic, or other suitable material which is capable of containing a gel or other suitable medium which allows the passage of ultrasound waves. The immersion bag 16 preferably has a general cylindrical shape for the greatest portion thereof and includes an end 30 which is dome shaped and an interior 32. The top of the immersion bag 16 is reversed a short distance outwardly and about itself to form a lip 34 of annular shape extending about the upper region of the immersion bag 16 for accommodation of the capture ring 22. The capture ring 22 is of annular shape fashioned of a flexible material, such as, but not limited to, rubber, latex, plastic or other suitable material.

Figure 3:
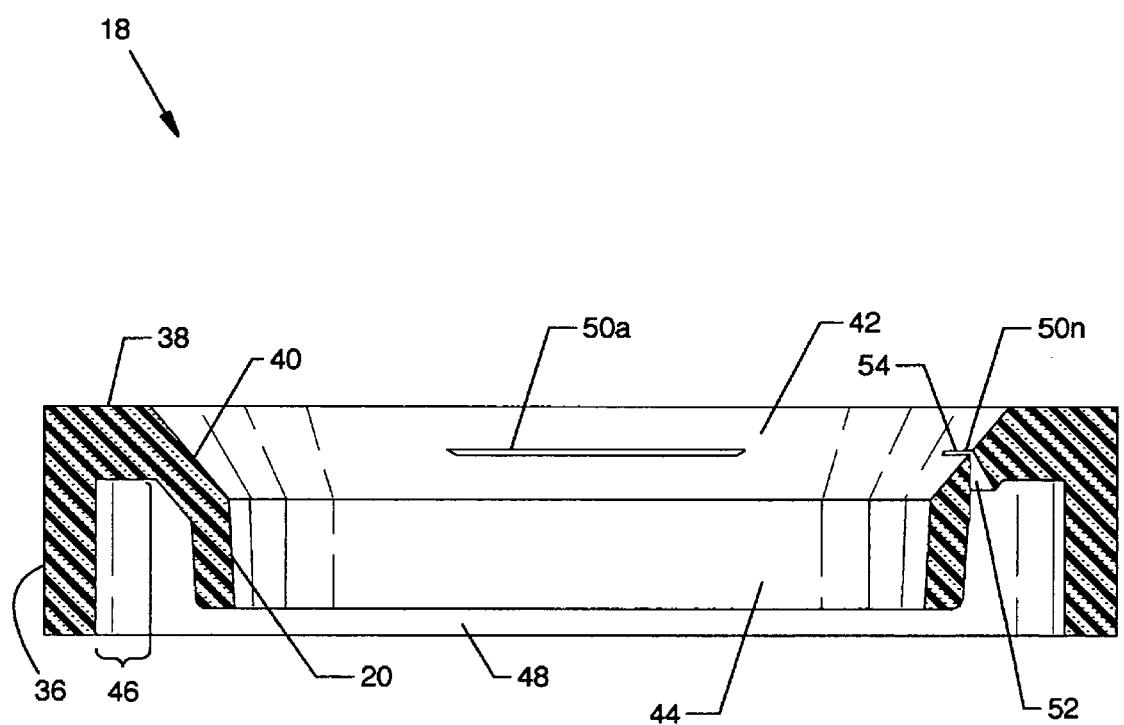
FIG. 3 is a cross section view of a one-piece flexible collar taken along line 3-3 of FIG. 4 in order to show both the general structure of the one-piece flexible collar and the structure of the valving extending through the wall thereof.
Figure 4:
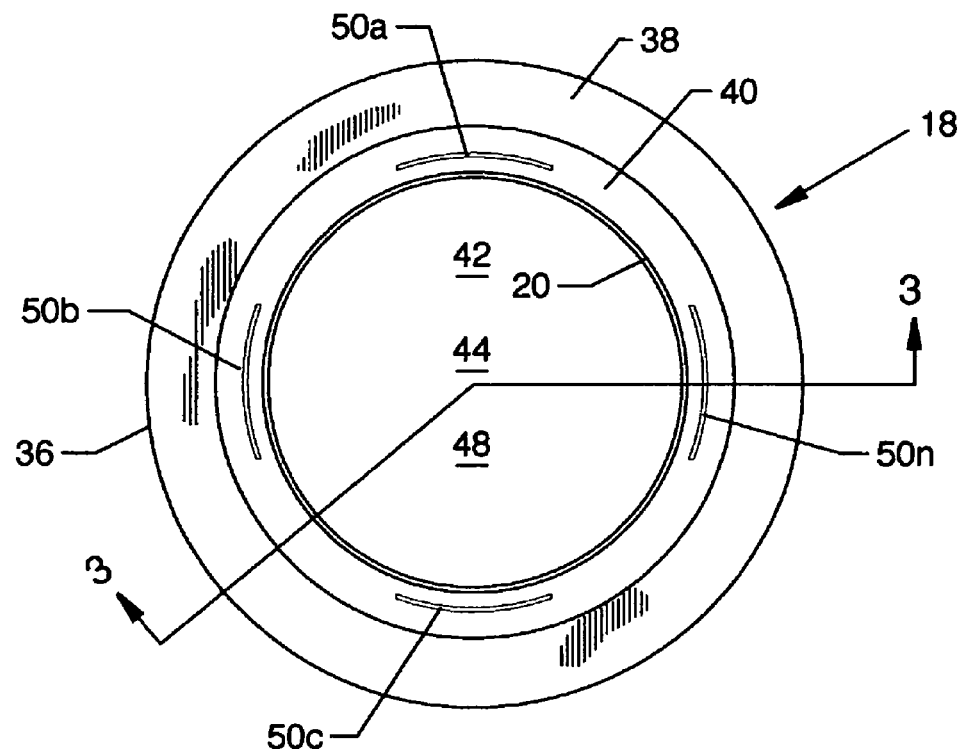
FIGS. 4 and 5 are top and bottom views, respectively, of the immersion bag one-piece flexible collar.
Figure 5:
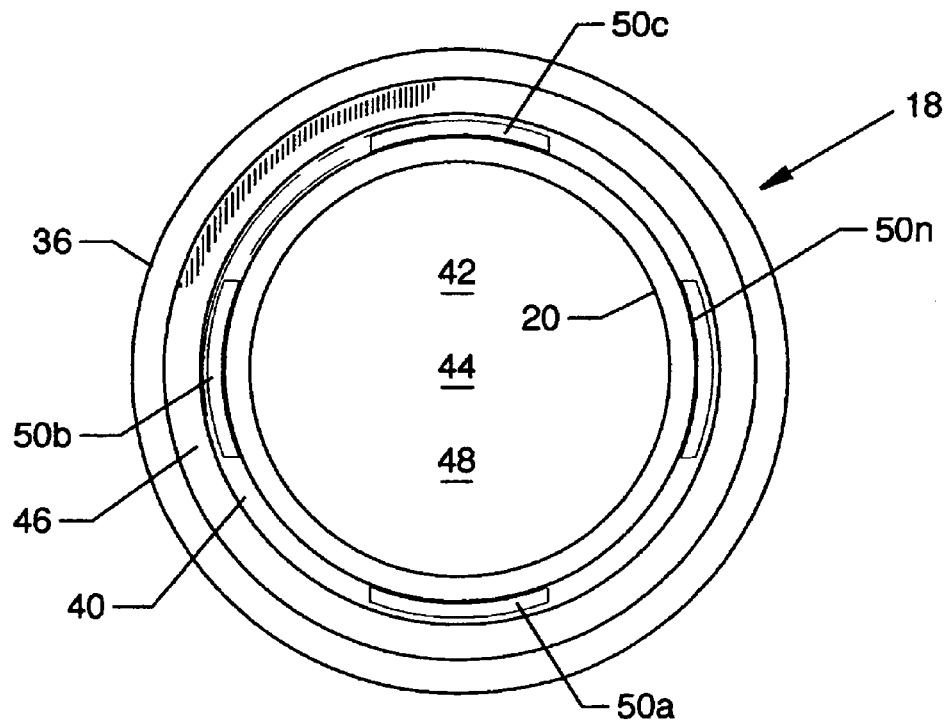
Figure 6:
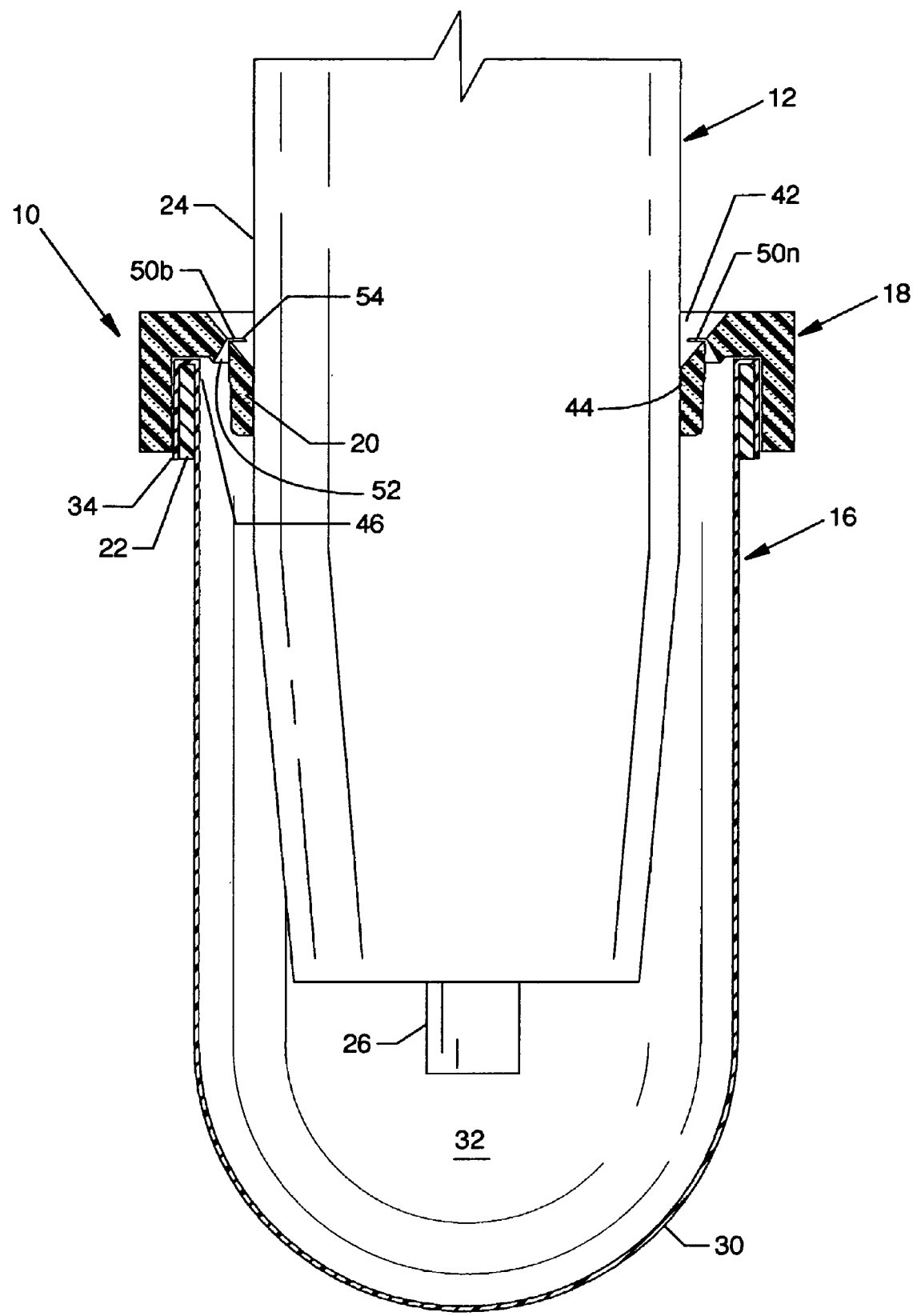
FIG. 6 is a partial cross section view showing engagement of an immersion bag system with the tip of an ultrasound probe.

FIG. 3 is a cross section view of the one-piece flexible collar 18 taken along line 3-3 of FIG. 4. The one-piece flexible collar 18, also shown in detail in FIGS. 4, 5 and 6, is of annular shape fashioned preferably of a flexible material such as foam, preferably closed cell foam, or of other suitable flexible and pliable material. The cross section view of FIG. 3 is taken along line 3-3 of FIG. 4 in order to show both the general structure of the one-piece flexible collar and the structure of the valving extending through the wall thereof. The continuously formed flexible collar 18 is comprised of a plurality of geometrically configured structures including: a vertically oriented outer wall 36 which forms the periphery of the flexible collar 18, a horizontally oriented top wall 38 which intersects the upper region of the outer wall 36 and extends inwardly a short distance, an angled transition wall 40 extending inwardly and downwardly from the top wall 38, and the seal 20 extending downwardly from the lower portion of the transition wall 40. The lower portion of the seal 20 is canted in slightly to ensure forcible flexed contact of the inner periphery of the seal 20 with the body 24 of the ultrasound probe 12. Other annular regions are formed by the previously described structure of the flexible collar 18 including a top opening 42 incorporating the angled inner periphery of the transition wall 40 as a guide structure for insertion of a probe body, such as the probe body 24, through the flexible collar 18, and a middle opening 44 formed by the inner periphery of the seal 20. A capture annulus 46 is formed near the junction of the inside surface of the outer wall 36 and the region underlying the top wall 38 for captured accommodation of the lip 34 of the immersion bag 16 in cooperation with the capture ring 22. An expansive bottom opening 48 is provided extending between the lower region of the capture annulus 46 and below the bottom edge of the seal 20 through which a probe body, such as the probe body 24, can pass unhindered. One or more self-sealing valves 50a-50n of arcuate and other structure are located along, about and extending through the transition wall 40. The cross section of the self-sealing valves 50a-50n, such as shown at self-sealing valve 50n, discloses a triangular shape having an elongated arcuate opening 52 at the outwardly facing surface of the transition wall 40 narrowing to a closed but actuable elongated arcuate slit 54 at the inwardly facing surface of the transition wall 40. The triangular shape extends as an extruded arcuate shape along a suitable arc, such as 20° for the purpose of example and illustration.

FIGS. 4 and 5 are top and bottom views, respectively, of the immersion bag flexible collar 18 including the seal 20. Shown in particular are the self-sealing valves 50a-50n in the flexible collar 18 and the annular structure of the flexible collar 18. The self-sealing valves 50a-50n vent the interior 32 of the immersion bag 16 when the tip of the ultrasound probe 12 is introduced into the interior 32 of the immersion bag 16. Air, gases, liquids, gels, or other mediums or fluids can be displaced or vented through the self-sealing valves 50a-50n during introduction of the tip of the ultrasound probe 12 or during further operation of the invention. The size of the self-sealing valves 50a-50n is shown in exaggerated form for purpose of illustration. In actual practice, the slits at the upper portions of the self-sealing valves 50a-50n, which alternatively can be in the form of narrow gaps or other suitable structure are parted by the force of the expelled or displaced air, gas, liquid, aqueous medium, gel, or the like, and modulate toward or to a closed state upon equalization between the immersion bag interior 32 and ambient pressure. The self-sealing valves 50a-50n could also be of different sized structure to operate across a pressure relief range. The purpose of the structure of the self-sealing valves 50a-50n is to prevent breakage of the immersion bag 16 by displacing air and to act as a fluid overflow. The self-sealing valves 50a-50n ensure adequate hydraulic force to remove wrinkles in the immersion bag 16 which result in acoustic artifacts (dead zones where shallow/superficial structures cannot be visualized).

FIG. 6 is a partial cross section view showing engagement of the immersion bag 16 with the tip of the ultrasound probe 12. The immersion bag system 10 shown includes the flexible collar 18 including the seal 20, the capture ring 22, and the immersion bag 16 fully arranged and assembled using the structural features of such components in suitable engagement made possible by the elastic qualities of the involved components in combination with the fixation of the lip 34 of the immersion bag 16 within the capture annulus 46 by the capture ring 22 using heat staking, adhesive or other suitable attachment. Additionally, the lip 34 of the immersion bag 16 is secured in the capture annulus 46 and sealingly held against the inner surface of the outer wall 36 by the forcible positioning of and the forcible engagement of the capture ring 22. The seal 20 flexes to sealingly accommodate and frictionally engage and seal against the body 24 of the ultrasound probe 12. The tip of the ultrasound probe 12 is positioned within the interior 32 of the immersion bag 16, wherein the transducer 26 is spaced sufficiently from the immersion bag end 30 to allow flexing of the bag end 30 about the surface of the eye and to prevent contact of the transducer 26 with the immersion bag end 30 during such flexing.

MODE OF OPERATION

Figure 7:
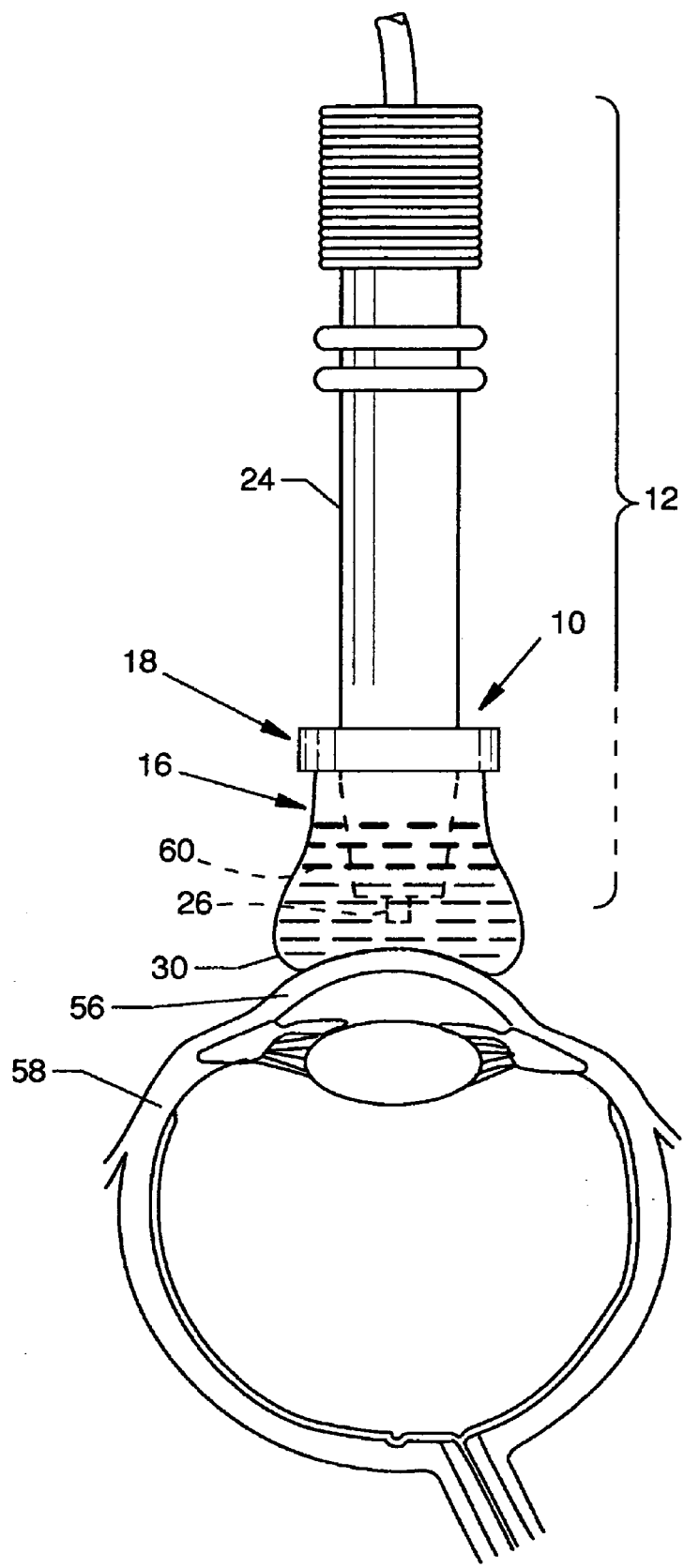
FIG. 7 illustrates an ultrasound probe with its tip surrounded by an immersion bag system contacting the cornea of an eye for performing an ultrasound scan of the central portion of the eye.
Figure 8:
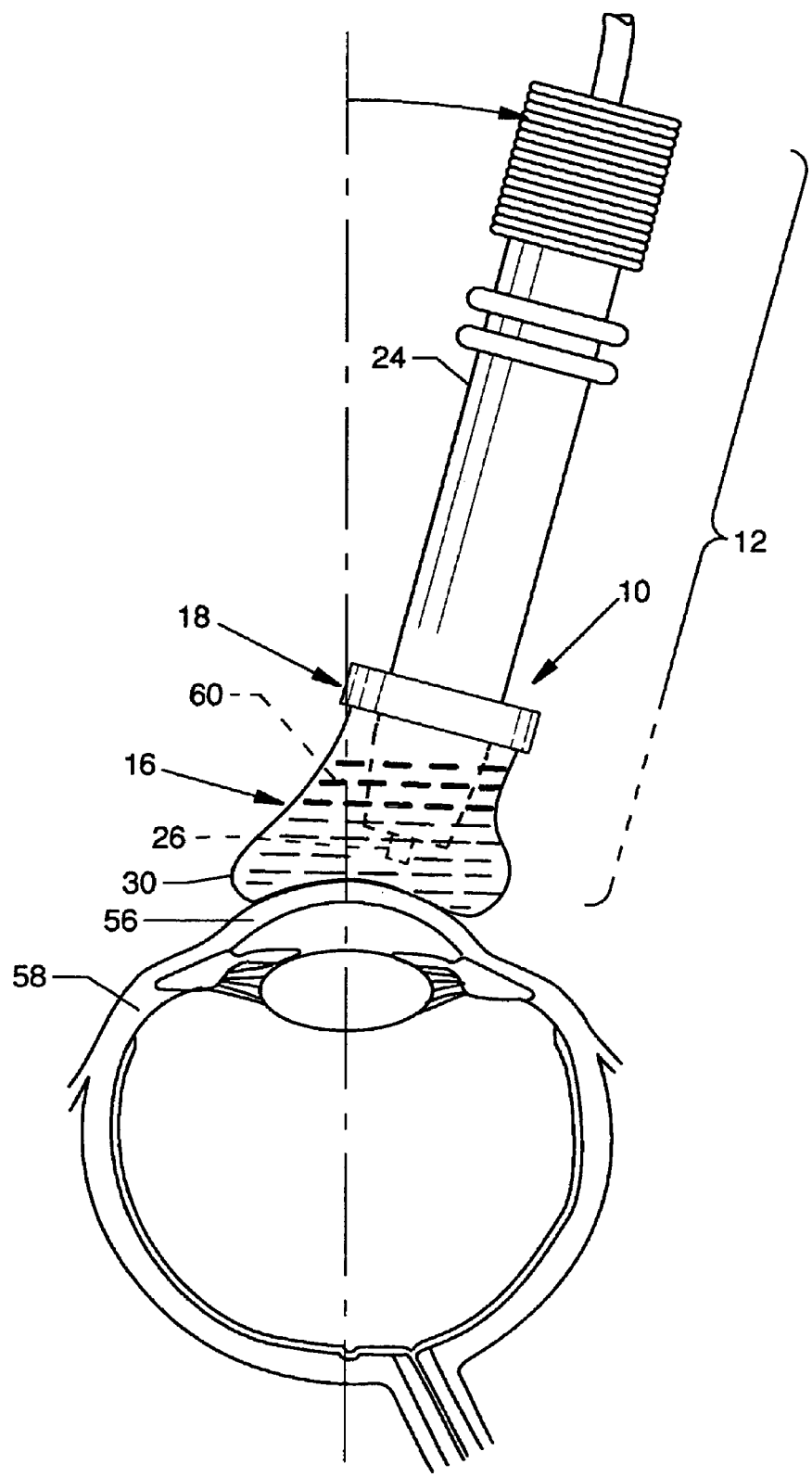
FIG. 8 illustrates an ultrasound probe with its tip surrounded by an immersion bag system engaging the cornea of an eye, the ultrasound probe being angled within the stationary but flexible immersion bag for an ultrasound scan of a non-central portion of the eye.

FIGS. 7 and 8 illustrate the immersion bag system 10 in use with an ultrasound probe 12 engaging a cornea 56 of an eye 58 for an ultrasound scan, e.g., of the central and non-central aspects of the eye 58, respectively. The immersion bag system 10 can be furnished as a sterile prepackaged disposable unit. The immersion bag 16 can be manually filled with a gel 60 or other suitable ultrasound transmission medium such as other aqueous medium, or the immersion bag 16 can be prefilled and covered by a removable top seal to contain the gel 60 or other aqueous medium within the immersion bag 16, wherein the top seal is removed prior to introducing the end of the probe body 24 into the flexible collar 18 and into the immersion bag 16. Also, a foil seal can hold an adequate amount of transducer coupling medium on the outside of the immersion bag 16. During introduction of the end of the probe body 24 into the flexible collar 18 and the immersion bag 16, the seal 20 flexingly seals against the body 24 of the ultrasound probe 12 to ensure that the gel 60 or other aqueous medium is contained within the interior 32 of the immersion bag 16. The previously described self-sealing valves 50a-50n are parted when the internal pressure of the immersion bag 16 exceeds a certain level in order to maintain the integrity of the immersion bag 16 and releases enough air, gas, liquid, gel, or other aqueous medium to reduce the internal pressure of the immersion bag 16 to a safe level and to prevent the bag from bursting but still have an internal positive pressure within the immersion bag 16. The ultrasound probe 12 is introduced a suitable distance (depending on probe frequency) into the interior 32 of the immersion bag 16 laden with gel 60 or other aqueous medium to overcome near field artifact where the transducer 26 preferably maintains a suitable spacing from the immersion bag end 30 and thus from the cornea 56 or other near surface. The invention comes in direct contact with the cornea 56 or other superficial structure, and upon initial contact, the bag end 30 of the immersion bag 16 intimately contacts and begins conformal reshaping to and about the surface of the cornea 56 or other superficial structure, while yet maintaining suitable spacing between the transducer 26 and the cornea 56 to overcome near field artifact. Also, the immersion bag 16 conforms to the surface under examination whether regular or irregular. The external ultrasound equipment is then energized after the ultrasound probe 12 is placed into the immersion bag 16 containing liquid/gel that has coupling fluid on the outside surface enabling an ultrasound scan of suitable width across the anterior aspects of the eye or other superficial structure. An ultrasound scan across a non-central portion of the eye 58 or other superficial structure can be accomplished, such as shown in FIG. 8, where the ultrasound probe 12 is repositioned to the side of the immersion bag 16 while maintaining the central original bag end 30 point of mutual contact. Contact with the examining surface remains in intimate contact due to the flexible nature of the immersion bag 16. Thus, there is minimal drag across sensitive and delicate structures such as the cornea, reducing the chance of abrasion. Although the invention is described for use with an eye, the principles of the invention also apply to use about other superficial areas of a body, whether human or animal, for ocular, cutaneous or vascular purposes, or inanimate objects, such as tubing carrying fluid. When the ultrasound probe 12 is inserted through the flexible collar 18, the seal 20 will be pulled downwardly, whereby this action will open one or more of the self-sealing valves 50a-50n. Thus, as the ultrasound probe 12 is moved into position as it is inserted into the immersion bag 16, slight positive pressure in the immersion bag 16 is maintained as the ultrasound probe 12 stops moving downwards but excess filler gel/liquid or air is simultaneously displaced.

Figure 9:
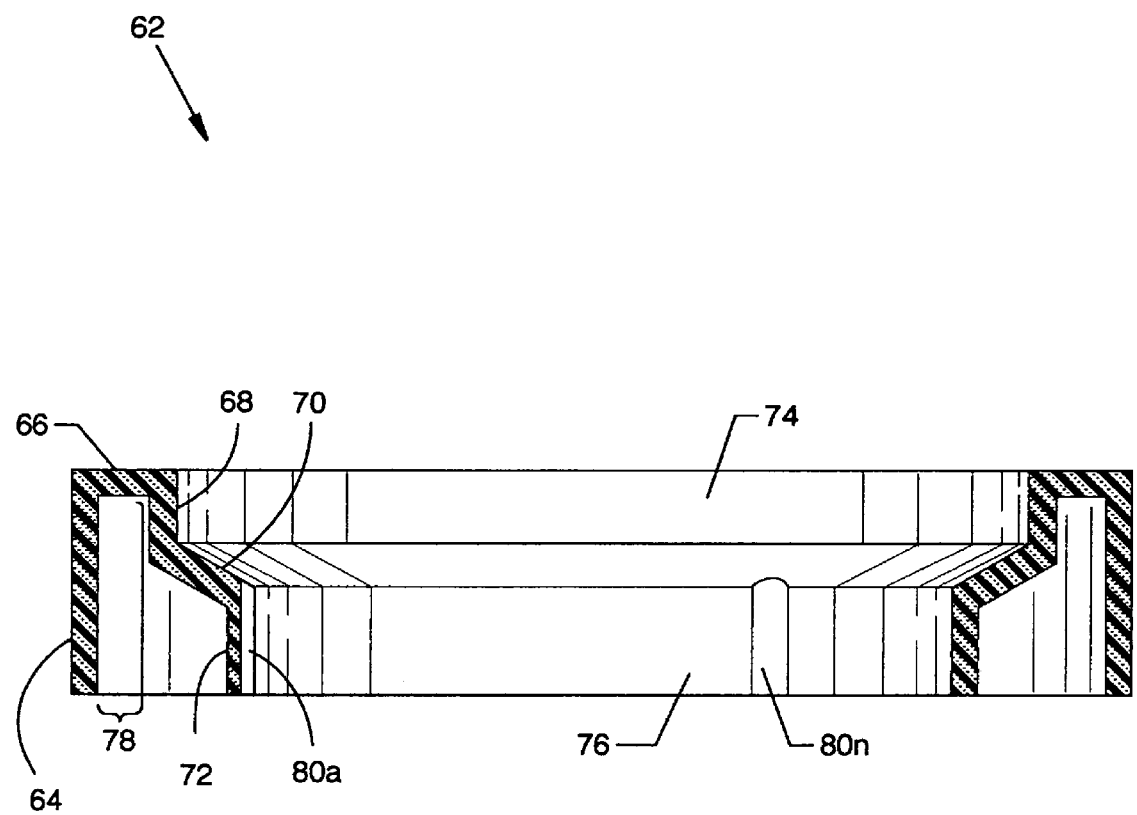
FIG. 9 is a cross section view of an alternative embodiment of a one-piece flexible collar taken along line 9-9 of FIG. 10.
Figure 10:
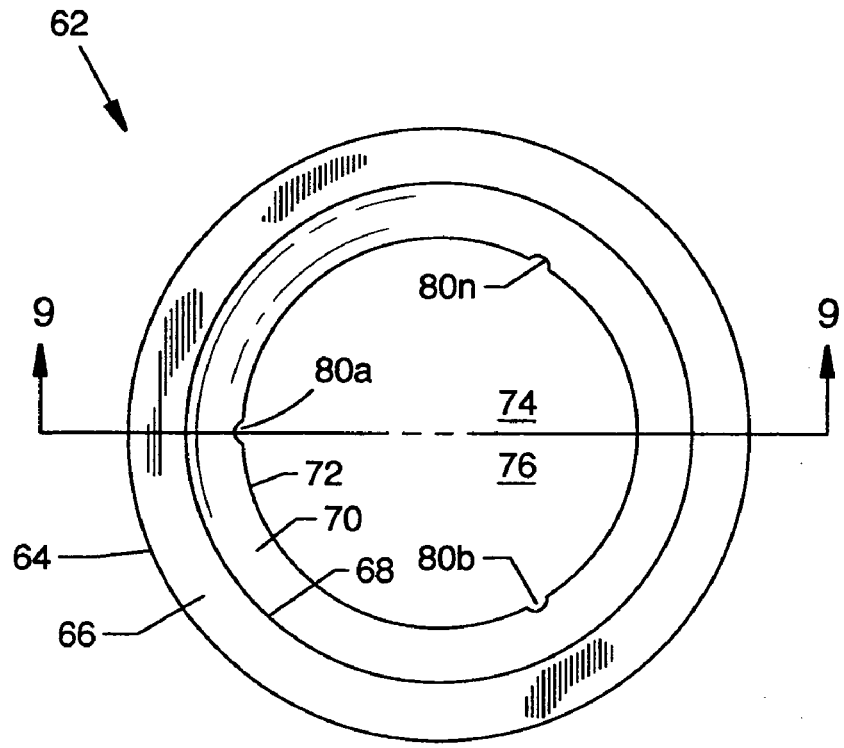
FIGS. 10 and 11 are top and bottom views, respectively, of the alternative embodiment one-piece flexible collar; and, FIG. 12 is a partial cross section view showing engagement of an immersion bag system using the alternative one-piece flexible collar with the tip of an ultrasound probe.
Figure 11:
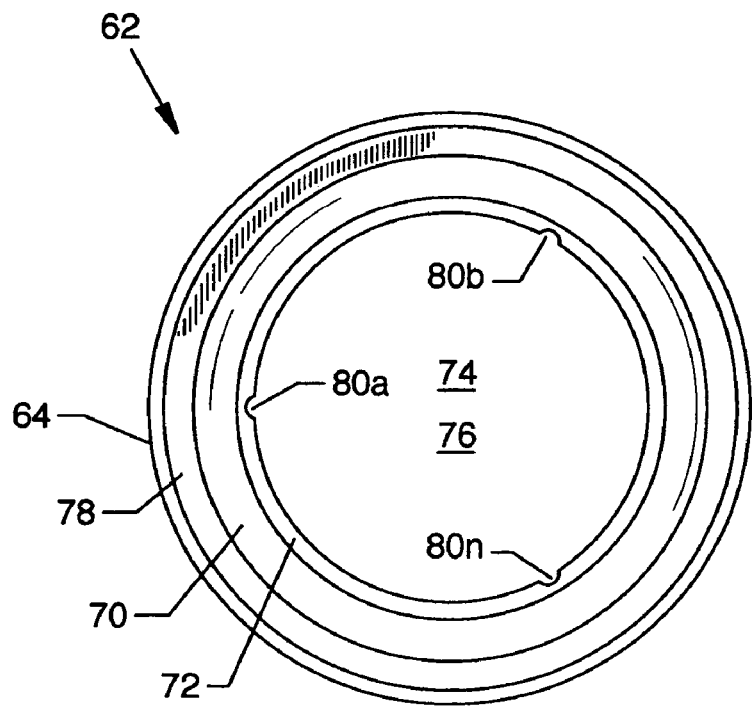

FIG. 9 is a cross section view of an alternative embodiment of a one-piece flexible collar 62 taken along line 9-9 of FIG. 10. The one-piece flexible collar 62, also shown in detail in FIGS. 10 and 11, is of annular shape fashioned preferably of a flexible material such as foam, preferably closed cell foam, or of other suitable flexible and pliable material. The cross section view of FIG. 9 is taken along line 9-9 of FIG. 10 in order to show both the general structure of the one-piece flexible collar 62 and the structure of the valving extending through the wall thereof. The continuously formed flexible collar 62 is comprised of a plurality of geometrically configured structures including: a vertically oriented outer wall 64 which forms the periphery of the flexible collar 62, a horizontally oriented top wall 66 which intersects the upper region of the outer wall 64 and extends inwardly a short distance, a vertically oriented the inner wall 68 extending downwardly from top wall 66, an angled transition wall 70 extending inwardly and downwardly from the lower portion of the inner wall 68, and a downwardly extending seal 72 extending from the angled transition wall 70. The lower portion of the seal 72 can be canted in slightly to ensure forcible flexed contact of the inner periphery of the seal 72 with the body 24 of the ultrasound probe 12. Other annular regions are formed by the previously described structure of the flexible collar 62 including a top opening 74 incorporating the angled inner periphery of the transition wall 70 and the inner periphery of the inner wall 68 as a guide structure for insertion of a probe body, such as the probe body 24, through the flexible collar 62, and a bottom opening 76 formed by the inner periphery of the seal 72. A capture annulus 78 is formed near the junction of the inside surface of the outer wall 64 and the region underlying the top wall 66 for captured accommodation of the lip 34 of the immersion bag 16 in cooperation with the capture ring 22. One or more self-sealing valves 80a-80n, preferably of arcuate structure, are located along, about and extending vertically through the inner face of the seal 72. The cross section of the self-sealing valves 80a-80n, such as shown at self-sealing valve 80a, discloses an elongated arcuate structure. The self-sealing valves 80a-80n are shown in the open position such as when venting excess pressures or fluid medium therethrough. In the non-venting position, the shape of the self-sealing valves 80a-80n would assume a flattened position but would modulate toward the open position, as shown, during release of pressure or of fluid medium.

FIGS. 10 and 11 are top and bottom views, respectively, of the immersion bag flexible collar 62 including the seal 72. Shown in particular are the self-sealing valves 80a-80n in the flexible collar 62 and the annular structure of the flexible collar 62. The self-sealing valves 80a-80n vent the interior 32 of the immersion bag 16 when the tip of the ultrasound probe 12 is introduced into the interior 32 of the immersion bag 16. Air, gases, liquids, gels, or other mediums or fluids can be displaced or vented through the self-sealing valves 80a-80n during introduction of the tip of the ultrasound probe 12 or during further operation of the invention. The size of the self-sealing valves 80a-80n is shown in exaggerated form for purpose of illustration. In actual practice, the self-sealing valves 80a-80n which alternatively can be in the form of narrow gaps, slits, other suitable structure, are parted by the force of the expelled or displaced air, gas, liquid, aqueous medium, gel, or the like, and modulate toward or to a closed state upon equalization between the immersion bag interior 32 and ambient pressure. The self-sealing valves 80a-80n could also be of different sized structure to operate across a pressure relief range. The purpose of the structure of the self-sealing valves 80a-80n is to prevent breakage of the immersion bag 16 by displacing air and to act as a fluid overflow. The self-sealing valves 80a-80n ensure adequate hydraulic force to remove wrinkles in the immersion bag 16 which result in acoustic artifacts (dead zones where shallow/superficial structures cannot be visualized).

Figure 12:
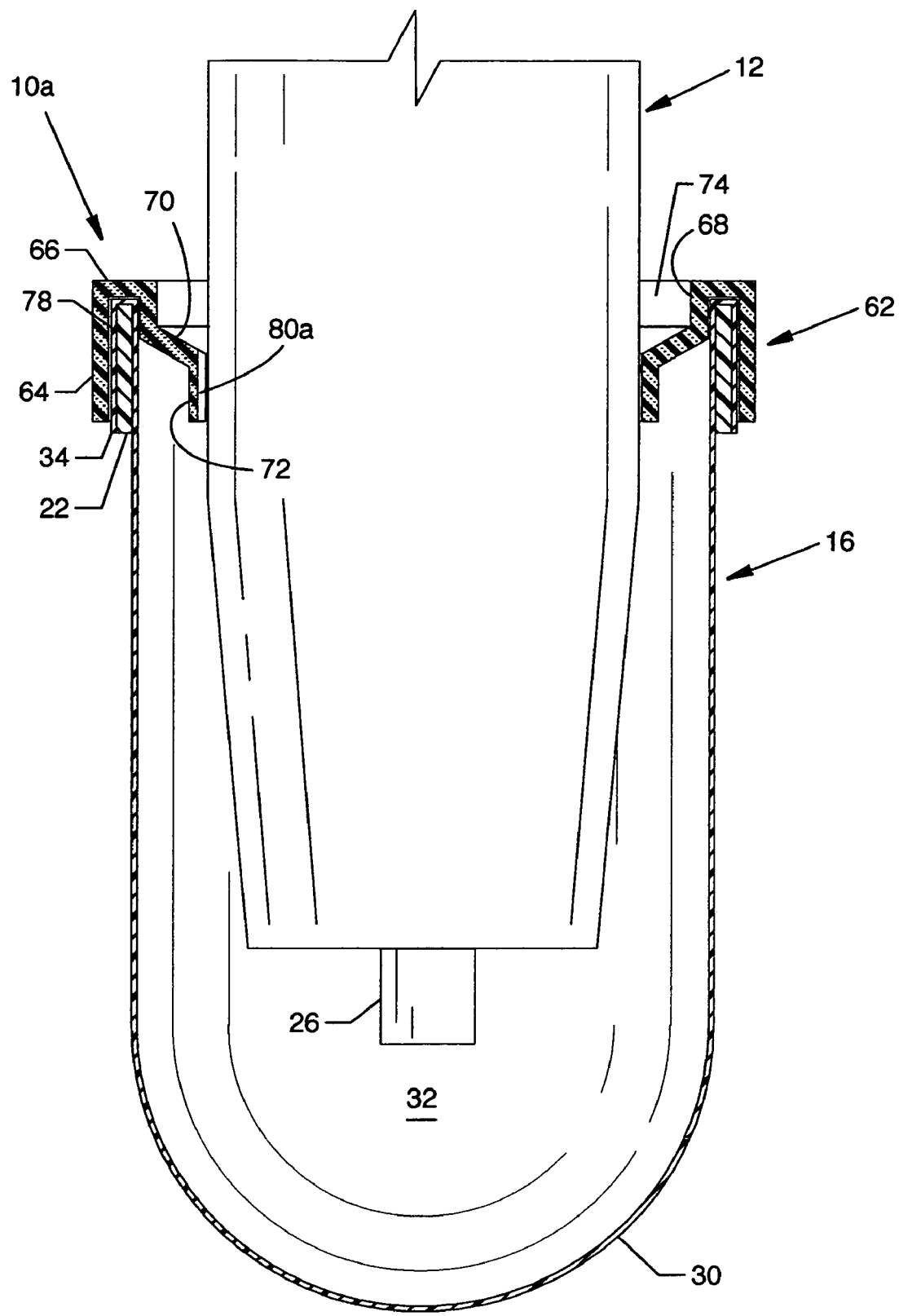

FIG. 12 is a partial cross section view showing engagement of an immersion bag system 10a with the tip of the ultrasound probe 12. The immersion bag system 10a shown includes the flexible collar 62 including the seal 72, the capture ring 22, and the immersion bag 16 fully arranged and assembled using the structural features of such components in suitable engagement made possible by the elastic qualities of the involved components in combination with the fixation of the lip 34 of the immersion bag 16 within the capture annulus 78 by the capture ring 22 using heat staking, adhesive or other suitable attachment. Additionally, the lip 34 of the immersion bag 16 is secured in the capture annulus 78 and sealingly held against the inner surface of the outer wall 64 by the forcible positioning of and the forcible engagement of the capture ring 22. The seal 72 flexes to sealingly accommodate and frictionally engage and seal against the body 24 of the ultrasound probe 12. The tip of the ultrasound probe 12 is positioned within the interior 32 of the immersion bag 16, wherein the transducer 26 is spaced sufficiently from the immersion bag end 30 to allow flexing of the bag end 30 about the surface of the eye and to prevent contact of the transducer 26 with the immersion bag end 30 during such flexing. The mode of operation of the immersion bag system 10a is substantially the same as described for the immersion bag system 10, the only difference being that the flexible collar 62 is substituted for the flexible collar 18. Although flexible collar 62 has been characterized as being an alternative to the flexible collar 18, neither collar is to be construed as being preferred over the other; both have equal stature.

Various modifications can be made to the present invention without departing from the apparent scope thereof.

PARTS LIST 10 immersion bag system
10a immersion bag system
12 ultrasound probe
16 immersion bag
18 flexible collar
20 seal
22 capture ring
24 body
26 transducer
28 control/power cable
30 end
32 interior
34 lip
36 outer wall
38 top wall
40 transition wall
42 top opening
44 middle opening
46 capture annulus
48 bottom opening
50a-n self-sealing valves
52 opening
54 slit
56 cornea
58 eye
60 gel
62 flexible collar
64 outer wall
66 top wall
68 inner wall
70 angled transition wall
72 seal
74 top opening
76 bottom opening
78 capture annulus
80a-n self-sealing valves

The invention claimed is:

1. An immersion bag system including an immersion bag, the immersion bag having an upper open end and a closed lower end and further having an attached flexible collar with an integral annular internal seal for sealing about the upper open end and a tip portion of an ultrasound probe, the integral annular internal seal having at least one self-sealing valve extending along, about and through the annular internal seal thereby providing a unidirectional air passage after the tip portion of the ultrasound probe is in place, thereby providing for the escape of air or liquid from within the immersion bag to limit the pressure therein and close upon partial or complete equalization between the immersion bag interior and ambient pressure.

2. The immersion bag system of claim 1, wherein a portion of the immersion bag may encapsulate the tip portion of the ultrasound probe.

3. The immersion bag system of claim 2, wherein the portion of the immersion bag which may encapsulate the tip portion of the ultrasound probe is acoustically transparent.

4. The immersion bag system of claim 1, wherein the attached flexible collar seal is compressible.

5. The immersion bag system of claim 1, wherein the immersion bag has a lip and further wherein the flexible collar of the immersion bag is attached to the lip by a capture ring.

6. The immersion bag system of claim 1, wherein the immersion bag may contact a cornea of an eye to allow ultrasound scanning of the eye.

7. The immersion bag system of claim 6, wherein the immersion bag may be positioned on a cornea to allow the ultrasound to scan a central portion of an eye.

8. The immersion bag system of claim 6, wherein an ultrasound probe sealed within the immersion bag system may be angled away from a cornea to scan a non-central portion of an eye allowing the examination of posterior structures through sclera of an eye.

9. The immersion bag system of claim 1, wherein the ultrasound probe tip portion includes a transducer, and further comprising liquid ultrasound transmission medium in the immersion bag, the ultrasound transmission medium separating the transducer from the immersion bag about an area being examined to overcome near field artifact.

10. The immersion bag system of claim 9, wherein the ultrasound transmission medium comprises a liquid of selected viscosities, and wherein the immersion bag system contains ultrasound transmission medium.

11. An immersed ultrasound system comprising:
   a. an ultrasound probe, the ultrasound probe having a body, a transducer on a lower region of the body and a control/power cable on an upper region of the body;
   b. an immersion bag system, the immersion bag system having an immersion bag, wherein the immersion bag includes an upper open end and a closed lower end and a flexible collar, an integral annular seal in the flexible collar for sealing about the upper open end, wherein the integral annular internal seal has at least one self-sealing valve extending along, about and through the annular internal seal thereby providing a unidirectional air passage, thereby permitting the escape of air or liquid from within the immersion bag to limit the pressure therein and close upon partial or complete equalization between the immersion bag interior and ambient pressure, and a capture ring; and,
   c. wherein the lower region of the ultrasound probe is sealed within the immersion bag and the immersion bag system is affixed to the lower region of the body of the ultrasound probe such that the transducer is immersed in an ultrasound transmission medium carried in the immersion bag and separates the transducer from the end tip of the immersion bag or anatomical structure.

12. The immersed ultrasound system of claim 11, wherein the lower region of the body of the ultrasound probe is generally tubular.

13. The immersed ultrasound system of claim 12, wherein the transducer is geometrically aligned with the generally tubular lower region of the ultrasound probe.

14. The immersed ultrasound system of claim 13, wherein the immersion bag system is frictionally engaged to the lower region of the ultrasound probe body.

15. The immersed ultrasound system of claim 14, wherein the integral seal of the flexible collar is annularly shaped.

16. The immersed ultrasound system of claim 11, wherein the integral seal of the flexible collar consists of a material selected from a group consisting of latex, rubber, foam, and plastic.

17. The immersed ultrasound system of claim 11, wherein the immersion bag consists of a thin and flexible pliable acoustically transparent material.

18. The immersed ultrasound system of claim 17, wherein the thin and flexible pliable acoustically transparent material is selected from a group consisting of polyethylene, polypropylene, polyurethane, and hydrophilic plastic.

19. The immersed ultrasound system of claim 17, wherein the thin and flexible pliable acoustically transparent material is capable of containing a gel, water, fluid of viscosities, or other suitable medium which allows the passage of ultrasound waves.

20. The immersed ultrasound system of claim 11, wherein the immersion bag has a generally cylindrical shape terminated by a dome shape.

21. The immersed ultrasound system of claim 20, wherein the immersion bag, having a generally cylindrical shape terminated by a dome shape further includes a top with an outward directed reverse about itself, defining an annular shaped lip extending about the upper region of the immersion bag, so as to accommodate the capture ring.

22. The immersed ultrasound system of claim 21, wherein the capture ring is annularly shaped.

23. The immersed ultrasound system of claim 22, wherein the capture ring is flexible.

24. The immersed ultrasound system of claim 23, wherein the capture ring consists of a material selected from the group consisting of rubber, latex, metal, and plastic.

25. The immersed ultrasound system of claim 11, wherein the one-piece flexible collar has an annular shape.

26. The immersed ultrasound system of claim 11, wherein the ultrasound transmission medium contained in the immersion bag, in contact with the transducer and wherein the ultrasound transmission medium separates the tip immersion bag from the transducer, such that the immersion bag may contact anatomy areas of a patient to enable a scan thereof by allowing conformational reshaping of the immersion bag where the immersion bag contacts the cornea.

27. The immersed ultrasound system of claim 26, wherein the ultrasound transmission medium is an aqueous medium.

28. The immersed ultrasound system of claim 27, wherein the aqueous ultrasound transmission medium is a gel of predetermined viscosities.

29. The immersed ultrasound system of claim 28, wherein the immersion bag system is supplied as a sterile pre-packaged disposable unit containing an ultrasound transmission medium with a removable top seal to retain the transmission medium prior to immersing the transducer on the lower region of the ultrasound probe therein.

30. The immersed ultrasound system of claim 29, wherein the integral seal is a self-sealing valve which limits internal pressure during immersion of the lower region of the probe and during contact with other anatomical areas.

31. A sterile pre-packaged disposable immersion bag system, for use with an ultrasound probe having a body, a transducer on a lower region of the body and a control/power cable on an upper region of the body, the immersion bag system comprising:
   a. an immersion bag, having a generally tubular shape with an upper open end and a domed lower end;
   b. a flexible collar with an integral annular seal in the flexible collar, the flexible collar surrounding the bag adjacent the upper open end, an integral annular seal in the flexible collar for sealing about the upper open end, wherein the integral annular internal seal has at least one self-sealing valve extending along, about and through the annular internal seal thereby providing a unidirectional air passage, thereby permitting the escape of air or liquid from within the immersion bag to limit the pressure therein and close upon partial or complete equalization between the immersion bag interior and ambient pressure;
   c. a capture ring, for sealing the upper open end of the immersion bag to the flexible collar;
   d. a removable top applied to the immersion bag adjacent the flexible collar and capture ring;
   e. an ultrasound transmission medium contained in the immersion bag by the removable top; and,
   f. wherein the lower region of the ultrasound probe may be sealed within the immersion bag upon immersion of the transducer and lower region of the body of the ultrasound probe into the ultrasound transmission medium in the immersion bag and the immersion bag system becomes affixed to the lower region of the body of the ultrasound probe such that the transducer is immersed in an ultrasound transmission medium carried in the immersion bag and separates the transducer from the immersion bag and from the anatomical structure under examination.

32. The sterile pre-packaged disposable immersion bag system of claim 31, wherein the integral seal is a pressure control valve for preventing excess pressure in the immersion bag during immersion of the transducer of the ultrasound probe.

33. The sterile pre-packaged disposable immersion bag system of claim 31, wherein the ultrasound transmission medium is an aqueous medium of selected viscosities.

34. A method of ultrasonic examination of an eye comprising the steps of:
   a. providing an ultrasound probe having a transducer;
   b. providing an ultrasound transmission medium to contact the transducer of the ultrasound probe;
   c. providing an immersion bag, having an interior and an exterior, to hold the ultrasound transmission medium in the interior of the bag, wherein the immersion bag includes an upper open end and a closed lower end and a flexible collar, an integral annular seal in the flexible collar for sealing about the upper open end, wherein the integral annular internal seal has at least one self-sealing valve extending along, about and through the annular internal seal thereby providing a unidirectional air passage, thereby permitting the escape of air or liquid from within the immersion bag to limit the pressure therein and close upon partial or complete equalization between the immersion bag interior and ambient pressure;
   d. immersing the transducer into the ultrasound transmission medium in the immersion bag;
   e. placing the exterior of the immersion bag against the eye or selected areas being examined with the ultrasound transmission medium in contact with the transducer of the ultrasound probe on the interior, such that the bag conforms to the external structure; and,
   f. scanning the eye or other structure through the ultrasound transmission medium with the immersion bag in contact with the anatomical areas.

35. The method of claim 34, wherein the ultrasound transmission medium is provided in the immersion bag as a pre-packaged sterile disposable kit, including a removable top.

36. The method of claim 34, wherein the immersion bag includes a flexible collar and capture ring, to affix the immersion bag to the ultrasound probe, the flexible collar further including a pressure relief mechanism.

37. The method of claim 36, wherein the pressure relief mechanism is a self-sealing valve in the flexible collar.

38. The method of claim 34, wherein the ultrasound transmission medium is an aqueous gel or aqueous solution of selected viscosities.

39. The method of claim 34, wherein the immersion bag is acoustically transparent.

40. The method of claim 34, wherein the immersion bag is tubular with a domed end and the domed end is in contact with the eye, thereby allowing central and non-central scanning of the eye due to conformance of the domed end of the immersion bag to the shape of the eye.

41. The method of claim 37, wherein the self-sealing valve in the flexible collar is able to create a distance standoff between the ultrasound probe transducer and the examining surface due to the created constant internal pressure within the bag resisting movement of the ultrasound probe toward the examined structural surface thereby overcoming the near field echo artifact.

42. The method of claim 37, wherein the self-sealing valve in the flexible collar maintains a constant level of positive internal bag pressure maintaining the appropriate ultrasound probe standoff distance, the probe from anatomical structure under examination, thus overcoming near field artifact.

* * * * *